(12) United States Patent
Kling et al.

(10) Patent No.: US 6,534,694 B2
(45) Date of Patent: Mar. 18, 2003

(54) ELASTIC STRUCTURE AND A DIAPER

(75) Inventors: Robert Kling, Skene (SE); Berth-Ove Wall, Landvetter (SE)

(73) Assignee: SCA Hygiene Products Aktiebolag, Gothenburg (SE)

( * ) Notice: Subject to any disclaimer, the term of this patent is extended or adjusted under 35 U.S.C. 154(b) by 0 days.

(21) Appl. No.: 09/984,506

(22) Filed: Oct. 30, 2001

(65) Prior Publication Data

US 2002/0156449 A1 Oct. 24, 2002

Related U.S. Application Data

(63) Continuation of application No. 08/597,377, filed on Feb. 8, 1996, which is a continuation of application No. 08/240,207, filed on May 9, 1994, now abandoned, which is a continuation of application No. 07/844,629, filed as application No. PCT/SE90/00631 on Oct. 2, 1990, now abandoned.

(30) Foreign Application Priority Data

Oct. 4, 1989 (SE) ............................................. 8903256

(51) Int. Cl.[7] .......................... A61F 13/15; A61F 13/20; B29C 65/08; B32B 31/00
(52) U.S. Cl. ............ 604/366; 604/385.25; 604/385.29; 604/385.3; 604/385.27; 604/369; 156/229; 156/253; 156/290
(58) Field of Search .............................. 156/73.1, 73.3, 156/163, 164, 229, 251–253, 290, 308.4, 309.6, 496, 494, 495, 513, 514, 515, 580.1, 292, 183, 197; 428/152; 604/358, 365–366, 378–382, 385.01, 385.24–385.3, 369, FOR 103, FOR 104

(56) References Cited

U.S. PATENT DOCUMENTS 3,563,822 A   2/1971   Fesh
3,817,802 A   6/1974   Meyer
3,844,869 A   10/1974  Rust, Jr.
4,081,301 A   3/1978   Buell
4,205,679 A   6/1980   Repke et al.
4,226,238 A   10/1980  Bianco (List continued on next page.)

FOREIGN PATENT DOCUMENTS

| EP | 0 023 804 | 2/1981 |
| EP | 0 184 072 | 6/1986 |
| FI | 86369 | 5/1992 |
| FI | 95995 | 1/1996 |
| GB | 2113983 | 8/1983 |
| GB | 2136677 | 9/1984 |
| GB | 2193100 | 2/1988 |
| SE | 436393 | 6/1979 |
| WO | WO 94/11189 A2 * | 5/1994 |

OTHER PUBLICATIONS

*Hawley's Condensed Chemical Dictionary*, Eleventh Edition, Van Nostrand Reinhold Company, New York, pp. 934–936.

Primary Examiner—Glenn K. Dawson
Assistant Examiner—K. M. Reichle
(74) Attorney, Agent, or Firm—Burns, Doane, Swecker & Mathis, L.L.P.

(57) ABSTRACT

A method of securing an elastic band between two material layers which are at least partially defined by meltable material includes forming perforations in the elastic band, placing the elastic band between two material layers, and bonding the material layers to one another through the perforations by heat fusion, wherein the perforations in the elastic band are formed at the same time as the material layers are fused together (i.e., the formation of the perforations in the elastic band is directly followed by bonding together, through the perforations, portions of the material layers). An elastic band secured between two material layers for inclusion in articles of one-time use includes the use of material layers that are at least partially defined by meltable material and an elastic band having perforations formed therein. The material layers are positioned on opposite sides of the elastic band and are joined together by heat fusion.

22 Claims, 8 Drawing Sheets

U.S. PATENT DOCUMENTS

| | | |
|---|---|---|
| 4,337,771 A | 7/1982 | Pieniak et al. |
| 4,397,645 A | 8/1983 | Buell |
| 4,404,052 A | 9/1983 | Persson et al. |
| 4,425,173 A | 1/1984 | Frick |
| 4,437,860 A | 3/1984 | Sigl et al. |
| 4,486,192 A | 12/1984 | Sigl |
| 4,573,991 A | 3/1986 | Pieniak et al. |
| 4,606,964 A * | 8/1986 | Wideman ................ 15/229.11 |
| 4,636,207 A | 1/1987 | Buell |
| 4,642,109 A | 2/1987 | Bradley et al. |
| 4,642,151 A | 2/1987 | Coenen |
| 4,657,539 A | 4/1987 | Hasse |
| 4,681,580 A | 7/1987 | Reising et al. |
| 4,695,278 A | 9/1987 | Lawson |
| 4,711,683 A | 12/1987 | Merkatoris |
| 4,718,901 A | 1/1988 | Singheimer |
| 4,720,415 A * | 1/1988 | Vander Wielen et al. ... 156/163 |
| 4,758,297 A | 7/1988 | Calligarich |
| 4,770,656 A | 9/1988 | Proxmire et al. |
| 4,770,657 A | 9/1988 | Ellis et al. |
| 4,816,026 A | 3/1989 | Richardson |
| 4,847,134 A * | 7/1989 | Fahrenkrug et al. ........ 156/163 |
| 4,904,251 A | 2/1990 | Igaue et al. |
| 4,908,247 A | 3/1990 | Baird et al. |
| 5,769,993 A * | 6/1998 | Baldauf ...................... 156/163 |
| 6,340,782 B1 * | 1/2002 | Kling et al. ................ 156/163 |

* cited by examiner

ELASTIC STRUCTURE AND A DIAPER

This application is a continuation of application Ser. No. 08/597,377 filed on Feb. 8, 1996, which is a continuation of application Ser. No 08/240,207 filed on May 9, 1994 (now abandoned), which is a continuation of application Ser. No. 07/844,629 filed on Apr. 1, 1992 (now abandoned), which was a national stage filing under 35 U.S.C. §371 of International Application No. PCT/SE90/00631 filed on Oct. 2, 1990, which international application was published by the International Bureau in English on Apr. 18, 1991.

FIELD OF THE INVENTION

The present invention relates to a method of securing elastic band between two layers of material which are made at least partially of meltable material. The invention also relates to an elastic band secured between two layers of material and intended for use in articles intended for one-time use only, such as disposable diapers, sanitary napkins, surgical dressings, protective clothing or the like, and also to a diaper which includes such an elastic band.

BACKGROUND OF THE INVENTION

In the manufacture of articles intended for one-time use only, such as disposable diapers or the like, it is desirable that these articles can be worn comfortably, will function effectively and fit properly, besides having an attractive appearance. These attributes are often compared with the attributes of corresponding multi-use articles. Such articles are traditionally manufactured from very soft, woven or knitted textile materials which are comfortable to wear and in which great care has been taken in cutting and sewing the materials from which the articles are made.

When manufacturing disposable articles, however, it is not possible to use expensive materials or to apply complicated and expensive manufacturing methods, since the articles would then demand an unreasonably high price. Instead, the traditional textile materials are usually replaced with plastic film, different types of non-woven fabric and tissue layers. Techniques such as gluing and welding are used, instead of sewing the articles together.

One particular problem in this respect is that of providing elastication edges, for instance elasticated leg, waist and sleeve bands. Normally, elastication in the form of elastic tape, bands or treads is secured along the edges of the article to be elasticated with the aid of melt adhesive. This method has several drawbacks, however. For instance, the glue has an uncontrollable stiffening effect on the elastic devices used, therewith impairing the elasticity of said devices. In the case of disposable diapers, for instance, the elastic devices, or elastication, is normally placed between two casing layers, normally a plastic film and a non-woven fabric layer. The elastic devices are mounted between the casing layers and fastened thereto while in a stretched state, whereafter the elastic devices return to their non-stretched, shorter state and gather together those parts of the casing layers to which the devices are attached. As a result, there is formed, primarily in the plastic film relatively sharp folds which are liable to chafe the skin of the wearer. Gluing of the elastic devices also causes the elasticated edge to become hard and chafing. These known elasticated edges are thus not as comfortable as would be desired.

Another drawback is that the formation of folds in the outer layers, or casing layers, results in the formation of channels between the elastic devices and the wearer's skin. This is particularly disadvantagous when the elastic devices are placed around the leg and waist parts of diapers, since these channels provide routes through which excreted body fluids can escape from the diaper. Neither can the known elastications be considered to satisfy the desire for an attractive, fabric-like appearance, but instead result in a wrinkled and shapeless finished article.

Difficulties are also experienced in the manufacture of articles where the elastication is glued thereto. The main problem is that the glue, which may be a melt glue or a thermosetting glue for instance, requires a certain amount of time for heating and cooling or drying the glue after it has been applied. During this time period, it is necessary to maintain the elastication in a stretched state, which presents a problem in a continuous manufacturing process. Furthermore, the necessity of handling a glue requires the provision of expensive special-duty equipment for avoiding troublesome occurrences, such as the adhesion of glue to machine rolls and knives.

Hitherto, it has not been found possible to provide in a simple and ready fashion elasticated edges which possess varying degrees of elasticity within different parts of the edges, or where certain parts of said edges are completely inelastic, various methods of providing elastication in limited areas, or with varying degrees of pretensioning, in a continuous manufacturing process have been proposed, for instance, in GB 2 113 983, EP 184 072, U.S. Pat. Nos. 4,642,151, 4,425,173, 4,486,192, 4,081,301, 4,711,683 and 4,642,109.

The present invention, however, now provides a simple method of securing an elastic band between two material layers comprised of at least partly meltable material while avoiding the drawbacks experienced with earlier known elastication.

SUMMARY OF INVENTION

The inventive method is may characterized m that perforations in the form of holes and/or slots are formed in the elastic band, in that the elastic band is placed between the two material layers; and in that material layers opposite said perforations are bonded together by heat fusion through said perforations.

The invention also relates to an elastic band secured between two material layers.

When such an elastic band is fastened onto an article which is intended for one-time use only, there is obtained a soft, non-chafing elastic edge. This is mainly due to the fact that no glue is used to fasten the elastication, but that the elastication is held mechanically between two mutually bonded material layers. Consequently, both the elastication and the material layers will retain their original softness and suppleness. This is also due to the fact that the elastic band can move to a certain extent in relation to the material layers surrounding said band, thereby enabling said layers to pleat or fold independently of one another when the elastic band relaxes. Distinct from the earlier known elastications, which gather the surrounding material layers into sharp, chafing folds, the material layers will form around an inventive elastic band soft, rounded folds which bulge outwardly from the elastication. This is because the material layers are bonded to the elastic band by mutually spaced bonds, those pats of the material layers located between the bonds are not bonded at all.

It should be mentioned that in the present context, the expression elastic band refers to an elongated elastic body whose width has a much-greater extension than the perforations formed therein in accordance with the invention.

A further advantage provided by an inventive elastic band resides in the possibility of achieving varying degrees of stretchability or elasticity within different regions of one and the same elastic band, simply by changing the bonding pattern. This feature is particularly useful in the case of all-in-one type diapers, for instance. Diapers of this kind comprise an absorbent pad which is enclosed between a liquid permeable, inner casing layer and a liquid-impermeable, outer casing layer or backing sheet. The elastication is normally applied along the edges of the absorbent pad, so as to form elasticated waist and leg edges. The diapers also include self-adhesive fastener tabs, which are attached to the corners of the diaper on the backed sheet, i.e. on that part of the diaper which is distal from the wearer in use. The tabs function to hold together the sides of the diaper, so as to obtain a trouser-like configuration around the abdomen of the wearer.

The fastener tabs are secured over the front part of the diaper, i.e. that part of the diaper which faces towards the wearer in use.

When securing the faster tabs, it is desirable that the surface of the diaper material are as smooth as possible. This applies particularly to that part of the front part of the diaper on which the fastener tabs are intended to be secured in use. If this part of the diaper is wrinkled and irregular, the fastener tabs will not grip securely and there is a risk that the diaper will not be held together during use. An advantage is also afforded when the tab rents on the rear part of the diaper have inelastic, smooth regions, since this facilitates securing of the tabs to the diaper during manufacture, and also provides more positive attachment of the fastener tabs. If the tape-fastening areas are elastic and the fastener tabs are secured to the diaper with the elastic devices in a stretched state, there is a serious risk that the tabs will loosen from the diaper when the elastic devices are relaxed from their stretched state and subsequently contract. The present invention, however, enables totally inelastic regions to be readily provided, by selecting an elastic-device bonding pattern such that the elastic devices are broken, down in these regions and loose their elasticity.

It is also possible to adjust the degree of elasticity around the leg openings of the diaper, for instance. The greatest elasticity is preferably found within those regions in which the elasic devices are attached to the crotch region of the diaper, i.e. that part of the diaper which, in use, is intended to lie between the wearer's thighs. On the other hand, there is preferably chosen in those parts of the elastic devices which extend along the front and rear portion of the diaper a bonding pattern which will reduce the elasticity of the elastic devices.

A further advantage afforded by an elastic band configured in accordance with the invention is that it imparts an aesthetically attractive, well-tailored appearance to the finished article. The elastic band appears soft and comfortable, whereby the finished article looks to be extremely comfortable, to the naked eye.

When an inventive elastic band is secured to the surrounding material layers at solely mutually spaced bonding locations, which permits the material layers to fold or pleat freely in relation to the elastic device, there is obtained an airy elastic edge and the soft material folds give a certain padding effect. The risk of the skin becoming irritated is very small, since the folds in the material layers bonded to the elastic band provide a certain ventilating effect, which will keep the skin beneath the elastic band substantially dry during use. The elastic band may also be made from an open-cell foam material, so as to provide air ventilation through the actual band itself, provided that at least one of the surrounding material layers is permeable to air.

A number of advantages are also obtained when manufacturing an elastic band in accordance with the invention. For instance, the troublesome handling of glue is avoided, as is also the need of drying or heating and cooling melt adhesive. Furthermore, there is avoided the need of complicated devices for varied stretching of the elastic devices, or of devices for handling pieces clipped from said elastic devices.

BRIEF DESCRIPTION OF THE DRAWING FIGURES

The invention will now be described in more detail with reference to exemplifying embodiments thereof illustrated in the accompanying drawings.

DETAILED DESCRIPTION OF THE PREFERRED EMBODIMENTS

Figure 1:
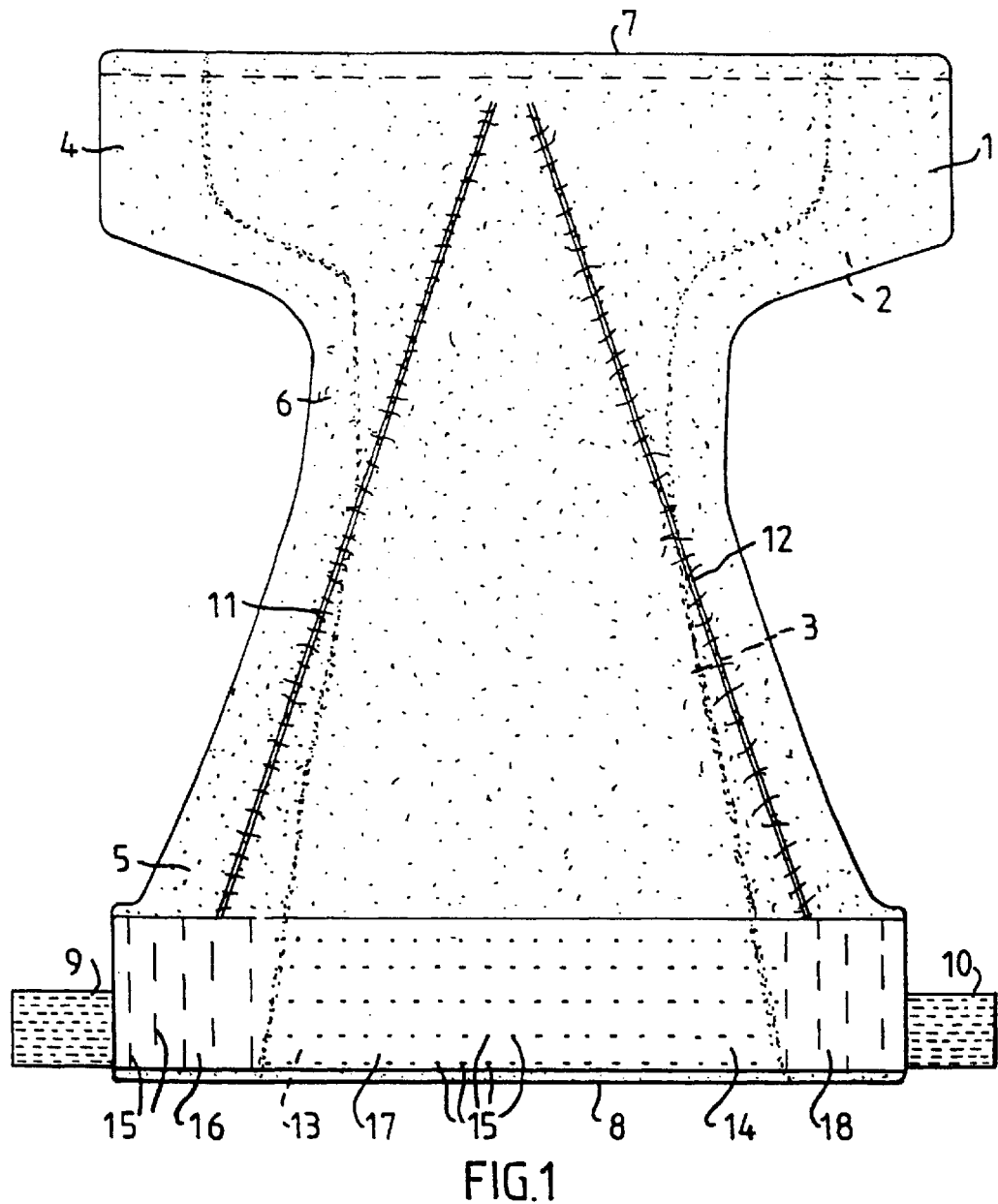
FIG. 1 illustrates a diaper according to a first embodiment of the invention, seen from the side which faces the wearer in use.

The diaper illustrated in FIG. 1 comprises a liquid-permeable casing layer 1, which is intended to face towards the wearer in use, a liquid-impermeable casing layer 2, which is distal from the wearer in use, and an absorbent pad 3 which is enclosed between the casing layers 1, 2. The liquid-permeable casing layer 1 preferably comprises some type of non-woven fabric or perforated plastic film, whereas the liquid-impermeable casing layer 2 may comprise, for instance, a liquid-impermeable plastic film or a hydrophobized non-woven fabric. When worn, the diaper is intended to embrace the lower abdomen of the wearer in a trouser-like fashion, and to this end has a front part 4 which is intended to be placed over the wearer's stomach in use, a rear part 5, which is intended to be placed over the wearer's bottom in use, and a narrower crotch part 6 which is located between the front part 4 and the rear part 5 and which is positioned between the wearer's thighs in use. Along its two short sides, the diaper also presents a front waist edge 7 and a rear waist edge 8, which together form the waist part of the diaper in use. Fastener tabs 9, 10 are disposed along the sides of the diaper rear-part 5, close to the rear waist edge 8. The tabs 9, 10 function to hold the diaper together to form a trouser-like configuration in use, and are therewith fastened to the front part of the diaper against the liquid-impermeable layer. To this end, the front part is preferably provided with a reinforcing layer, within the region in which the tabs shall be fastened. The reinforcing layer may consist, for instance, of a polypropylene plastic strip and functions to enable the tabs to be refastened. The edges of the diaper define diaper margins.

Elastic devices 11, 12, for instance in the form of elastic bands or yarn-spun threads, extend from the centre of the front waist edge 7 of the diaper in a V-shaped pattern towards the rear waist edge 8 of said diaper. The elastic devices 11, 12 can be attached to the diaper by welding or gluing. A further elastic device 13 in the form of a broad rubber band or a band made of elastic foam material extends along the rear waist edge 8, between the two fastener tabs 9, 10. When the diaper is worn, the elastic devices 11, 12, positioned in a V-shaped pattern, form the elastication around the edges of the diaper legs, whereas the elastic device 13 attached along the rear waist edge 8 forms the elastication around the edge of the waist part of the diaper. This latter elastic device is placed within a casing 14 of heat-meltable fabric surrounding said device, and is secured to the casing at discrete bonding locations 15.

The elastic device 13 is divided into three separate regions 16, 17, 18, having mutually different bonding patterns. A first bonding pattern, in which the bonding locations 15 have the form of discontinuous lines extending transversely to the direction in which the device 13 acts, is disposed in the two regions 16, 18 which lie closest to the fastener tabs. In the region 17 at the centre part of the elastic device 13, the bonds are disposed in punctiform rows instead.

The bonds located in said region 17 cover a smaller area of the elastic device 13 than the bonds located within the regions 16, 18 nearest the fastener tabs 9, 10, and have a small extension transversely to the direction in which the elastic device 13 acts. In this way, the elastic device 13 will retain essentially the same degree of elasticity within this region 17 as in its non-bonded state.

Within the regions 16, 18 located nearest the diaper fastener tabs 9, 10, where the bonds are disposed with small extension in the action direction of the elastic device, but extend substantially perpendicularly to said direction, the bonded elastic device 13 has lost practically all of its elasticity. The greater bonding density within these regions 16, 18 also contributes to reducing the elasticity of the device 13. As before mentioned, the inelastic regions 16, 18 are intended to ensure that the tabs 9, 10 will fasten effectively.

The arrangement of bonding regions in the form of broken lines avoids the occurrence of channels which extend transversely across the full width of the elastic device and through which liquid is able to run when the diaper is worn. Instead, discontinuous folds are formed in the casing 14 around the elastic device 13, these folds preventing the through-passage of liquid but permitting air and water vapour to pass there-through.

As illustrated in FIG. 1, the elastic band 13 with surrounding casing 14 is attached to the liquid-permeable casing layer 1 of the diaper while in a stretched state, for instance with the aid of ultrasonic welding techniques. If the elastic band is manufactured separately, outside the diaper manufacturing line, the actual attachment of the band is effected in the elastic region 16, 18, whereas only a few attachment points are used in the region 17, therewith not to reduce the elasticity of the band and to ensure that no space is formed between the band 13 and the casing layer 1 when the band contracts in this region in the finished product. According to one preferred embodiment, the band 13 will have an incomplete bonding pattern when applied to the casing layer 1, and the bonding pattern is completed by fastening the band to said casing layer. Naturally, the band can also be glued filmy to the casing layer, in which case only a few glue points, or preferably longitudinally extending glue beads will occur in the region 17.

Figure 2:
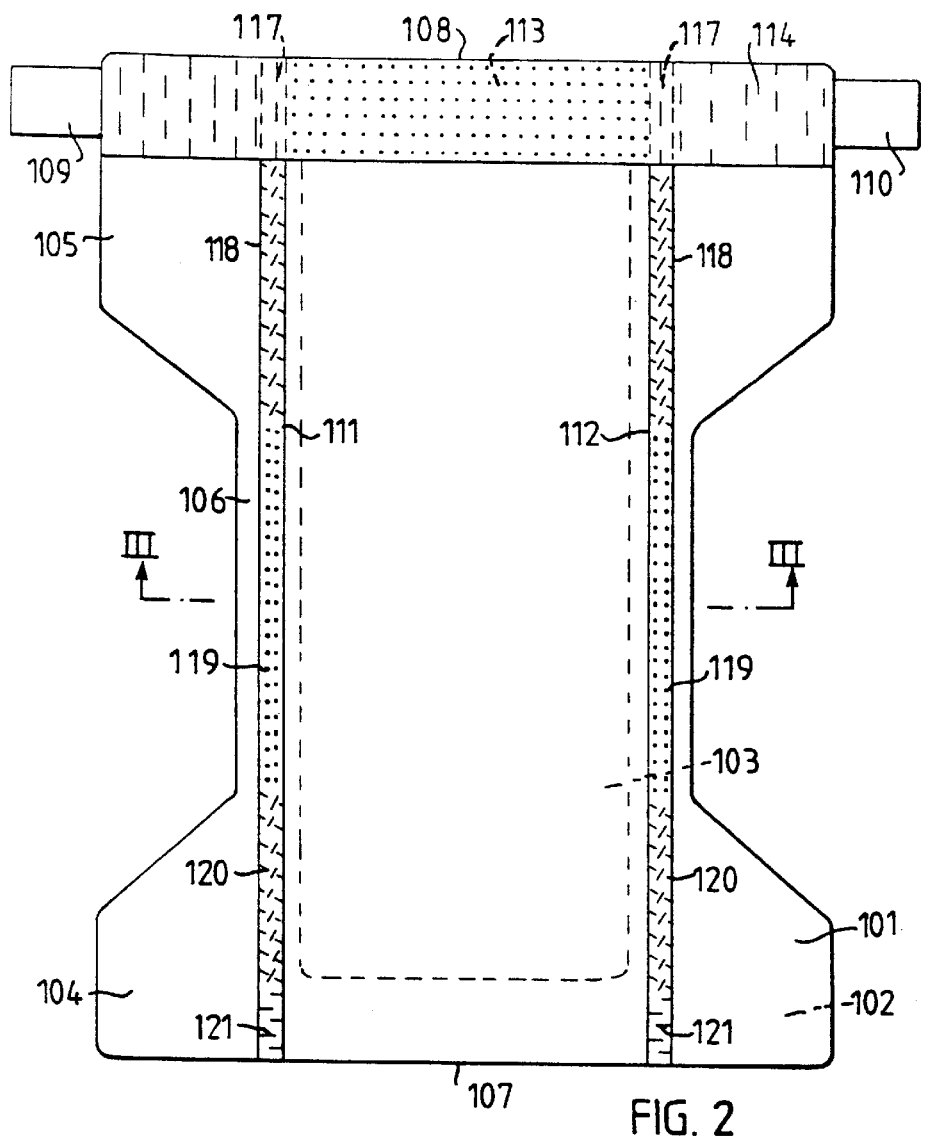
FIG. 2 illustrates a diaper according to a second embodiment, seen from the side which faces the wearer in use.

The diaper illustrated in FIG. 2 is constructed in essentially the same manner as the diaper illustrated in FIG. 1 and includes a liquid-permeable casing layer 101, a liquid-impermeable casing layer 102, and an absorbent pad 103 enclosed between said casing layers.

Figure 3:
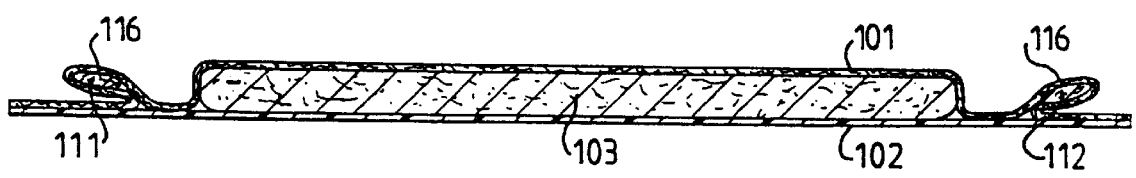
FIG. 3 is a sectional view taken on the line III—III on the diaper of FIG. 2.

The diaper has an hour-glass configuration and, similar to the diaper of FIG. 1, has a front part 104, a rear part 105, a crotch part 106, and a front and a rear waist edge 107, 108. Diaper fastener tabs 109, 110 are provided on the side edges of the rear part 105, close to the rear waist edge 108. An elastic device 113 is attached along the rear waist edge 108, within a nonwoven fibre casing 114, with a bonding pattern corresponding to the diaper illustrated in FIG. 1. The diaper illustrated in FIG. 2 also includes two further elastic devices 111, 112 of the same kind as the first elastic device, but position in the longitudinal direction of the diaper on either side of the absorbent pad 103. These devices 111, 112 are intended to provide the diaper leg elastication. The devices are enclosed in longitudinally extending folds 116 in the liquid-permeable casing layer 101 of the diaper, as will best be seen from FIG. 3. Similar to the diaper illustrated in FIG. 1, the elastic devices 111, 112 are secured within the folds 116 by ultrasonic welding, wherein the ultrasound perforates the elastic devices 111, 112 in a predetermined pattern and fuses together the surrounding casing parts 114 through the perforations. Each of the elastic devices 111, 112 presents five regions 117–121 having three mutually different bonding patterns and different degress of elasticity. The greatest elasticity is found in the elastic devices 111, 112 within the crotch part 106 of the diaper, where the bonding pattern consists of discrete, punctiform bonds. A bonding pattern in the form of broken, transverse lines has been used within the regions 117, 121 nearest the waist edges 107, 108. As before mentioned, this bonding pattern causes the elastic devices 111, 112 to be practically inelastic within these regions.

The elastic devices 111, 112 are bonded with a pattern of intersecting, broken, oblique lines in those regions 118, 120 located between the inelastic regions 117, 121 at the waist edges 107, 108 of the diaper and the regions 119 in the crotch part 106 thereof. This bonding pattern results in a lower elasticity than the punctiform bonds at the crotch part of the diaper, but in greater elasticity the traverse bonds at the waist edges of the diaper.

FIGS. 4–8 illustrates examples of methods of sewing an inventive elastic device to one edge of a diaper or to some other absorbent product. Corresponding elements in the Figures have been identified with the same reference signs. In all of the embodiments illustrated in FIGS. 4–8, the elastic device consists of an elastic strip of open-cell foamed plastic.

Figure 4:
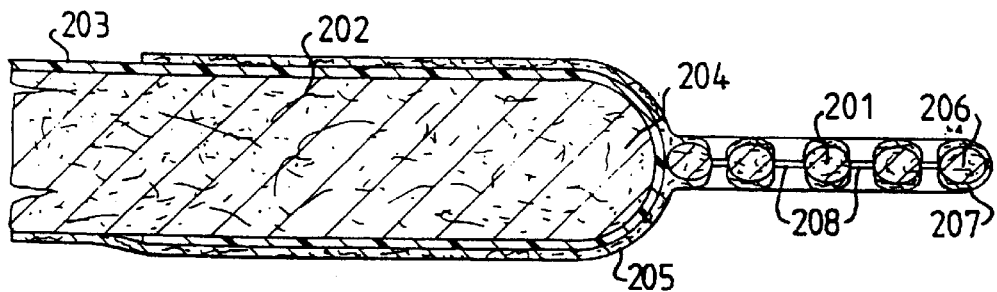
FIGS. 4–8 illustrates different methods of applying an inventive elastic device to the edge of an absorbent article.

The elastic device 201 illustrated in FIG. 4 is attached in the extension of an absorbent pad 202, which has a liquid-impermeable layer 203 attached to one side thereof, i.e. the outwardly facing side thereof. The liquid-impermeable layer is folded around the edge pat 204 of the absorbent pad, so as to prevent the leakage of fluid past said edge. A liquid-permeable layer 205, for instance a polypropylene non-woven fabric layer, is attached to the other side, the inwardly facing side, of the absorbent pad 202. The liquid-permeable layer 205 extends beyond the absorbent pad 202 and over the elastic device 201, and is folded back around the free edge 206 of said device and fastened, e.g. with the aid of melt adhesive, to the liquid-impermeable layer 203 on the outer side of the absorbent pad 202. The elastic device 201 is thus enclosed in a fold 207 located externally of the absorbent pad 202 in the liquid-permeable layer 205 and is secured within the fold 207 at discrete bonding locations 208, in accordance with the invention.

Figure 5:
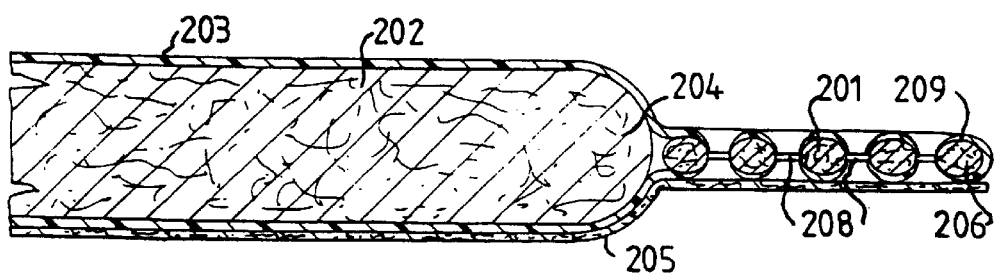

In the embodiment illustrated in FIG. 5, the elastic device 201 is secured within a fold 209 in the liquid-impermeable layer 203, located externally of the edge 204 of the absorbent pad. This layer 203 normally comprises plastic film and in order to avoid contact between the plastic film and the wearer's skin in use, the liquid-permeable layer 205 extends on the inside of the diaper completely past the edge 204 of the absorbent pad, to the free edge 206 of the elastic device.

Figure 6:
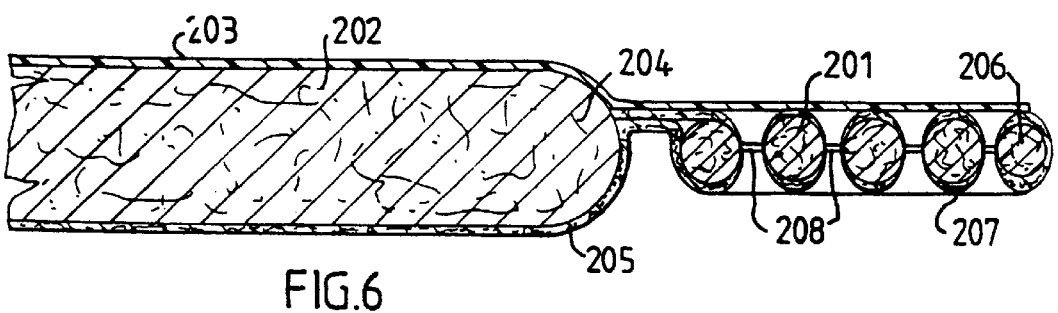

FIG. 6 illustrates a further example of a method of securing the elastic device 201 within a fold 207 in the liquid-permeable layer 205. The liquid-permeable layer 205 extends beyond the absorbent pad 202 and is folded around the elastic device 201, without being folded back across the pad 202. The liquid-impermeable layer 203 extends on the outside of the pad 202 up to the free edge 206 of the elastic device. An extremely effective leak-proof construction is achieved in this way.

Figure 7:
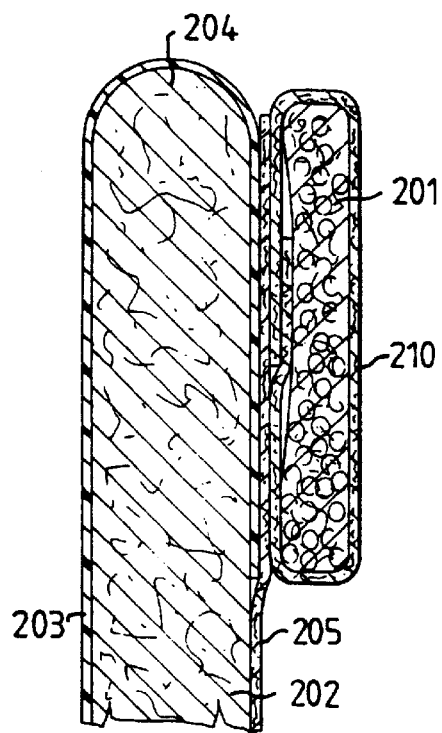

The elastic device 201 illustrated in FIG. 7 is secured within a casing 210 of heat-meltable non-woven fabric. The device 201 with surrounding casing 210 is attached to the liquid-permeable layer 205 on the inside of the pad 207 and inwardly of the edge 204 of said pad.

Figure 8:
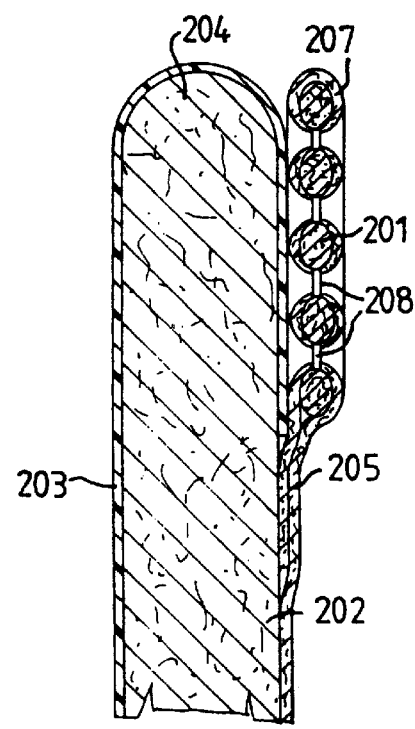

The elastic device 201 illustrated in FIG. 8 is also secured inwardly of the edge 204 of the absorbent pad. In this embodiment, however, the device 201 is secured within a fold 207 in the liquid-permeable layer 205. The liquid-impermeable layer 203 in FIGS. 7 and 8 is folded around the edge 204 of the absorbent pad in the same manner as in the FIG. 4 embodiment.

Figure 9:
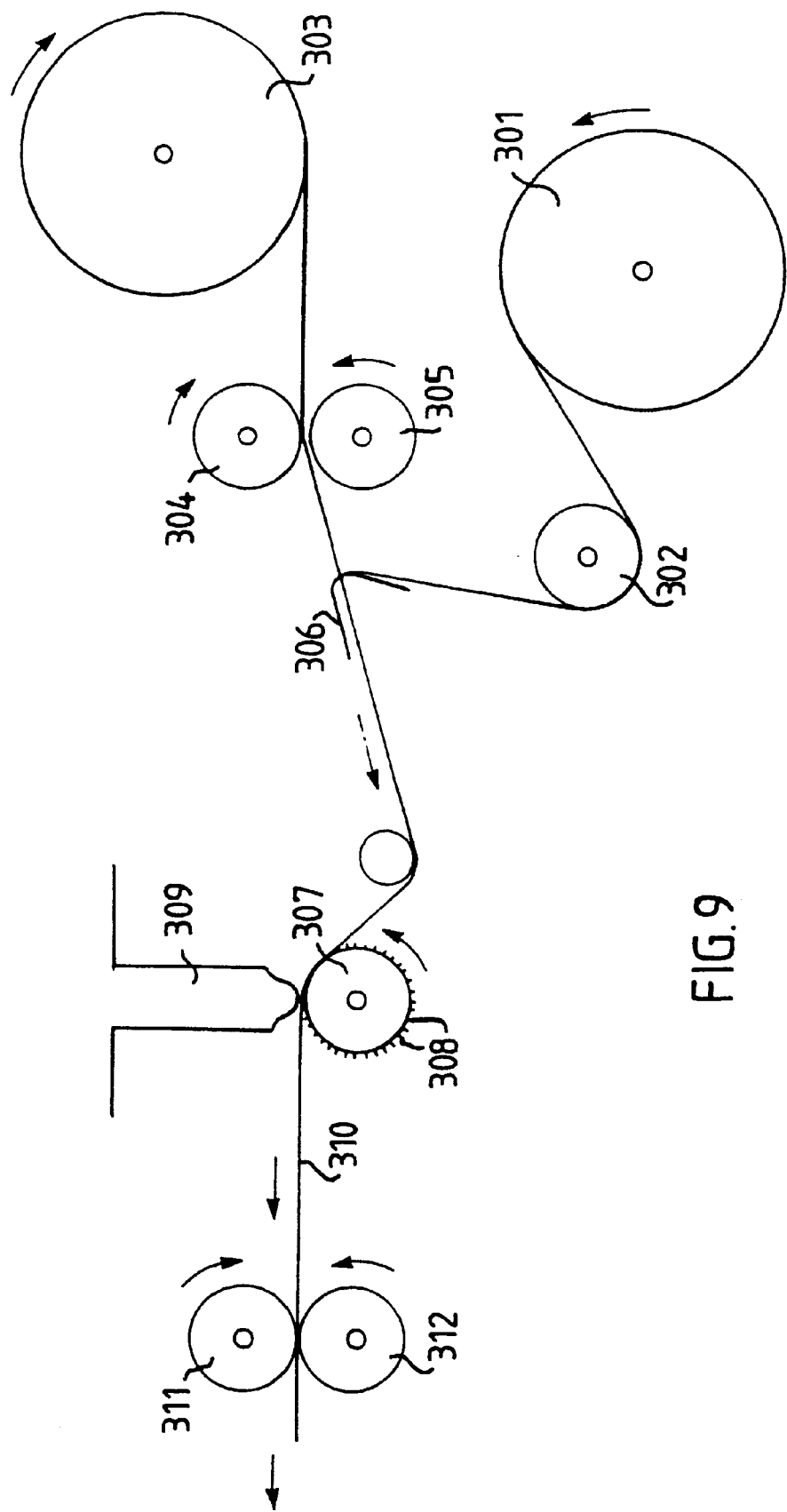
FIG. 9 illustrates schematically a process for the manufacture of an inventive elastic device.

An inventive elastic device can be secured within a casing in the manner illustrated schematically in FIG. 9. A heat meltable casing material 301, for instance in the form of non-woven fabric or plastic film, extends from a first reel of material, via a guide roller 302. At the same time, a band 303 of elastic material is fed from a second reel while passing between a first pair of rollers 304, is 305, whereafter the casing material 301 is folded around the elastic band 303 by means of a folding plate 306, such that both sides of the band 303 are covered by the casing material 301. The band 303, together with the surrounding casing 301, is then transported over a patterned bonding roller 307. The bonding roller 307 presents raised portions or devices 308 which correspond to the desired bonding pattern of the finished elastic laminate. Bonding is effected with the aid of an ultrasonic horn 309. The ultrasound perforates the elastic band and fuses the casing material together through the perforations thus formed. That is, the perforations are formed in the elastic bond directly followed by bonding together, through the perforations, the portions of the casing located opposite the perforations. The bonding pattern is predetermined and, as before mentioned, is controlled by the raised portions or devices 308 on the bonding roller. The resultant, bonded elastic laminate 310 is then advanced by a second pair of rollers 311 and 312 which are driven at a second speed which is higher than the speed at which the first roller pair 304, 305 is driven. Because the second roller pair 311, 312 is driven at a higher speed than the first roller pair 304, 305, the elastic band 303 will be stretched before it is bonded within the heat-meltable casing 301. The elastic band can be uniformly stretched to pretension the elastic bands.

The elasticity of the finished laminate 310 can be controlled in two ways. By selecting a given ratio between the speeds at which the first roller pair 304, 305 and the second roller pair 311, 312 are driven, it is possible to impart to the elastic laminate 310 a given maximum elasticity or basic elasticity. By using different bonding patterns for different parts of the elastic band, it is possible to reduce to varying high degrees the basic elasticity determined by the speeds at which said roller pairs are driven. The finished elastic laminate 310 will thus present parts of mutually different elasticity.

In order to illustrate how elasticity is affected by the bonding pattern, tests were carried out on two laminate samples having mutually different bonding patterns. The elastic devices used in both samples had a width of 50 mm and a thickness of 2 mm and comprised a band of flexible, polyurethane foam based on polyester. The elastic foam material is retailed by CIRRUS A/S, Denmark, under the designation 2 130 170. The elastic band was enclosed in a non-woven fabric casing or envelope in the manner described with reference to FIG. 9. The band was therewith stretched 70%, meaning that the ratio between the first driving speed and the second driving speed was 1.70. The non-woven fabric casing used comprise heat-bonded polypropylene fibres.

Figure 10:
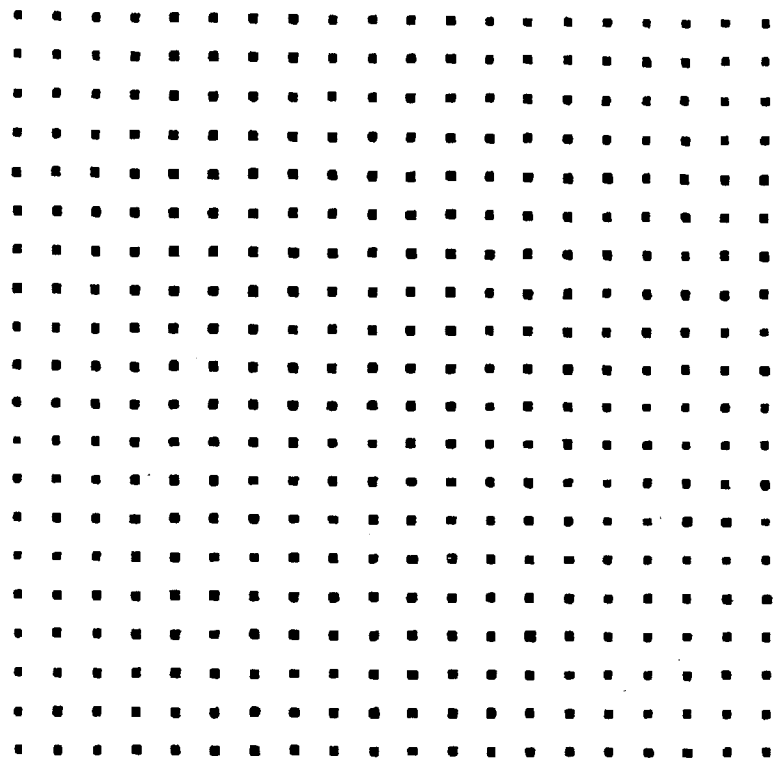
FIGS. 10 and 11 illustrate different bonding pattern.
Figure 11:
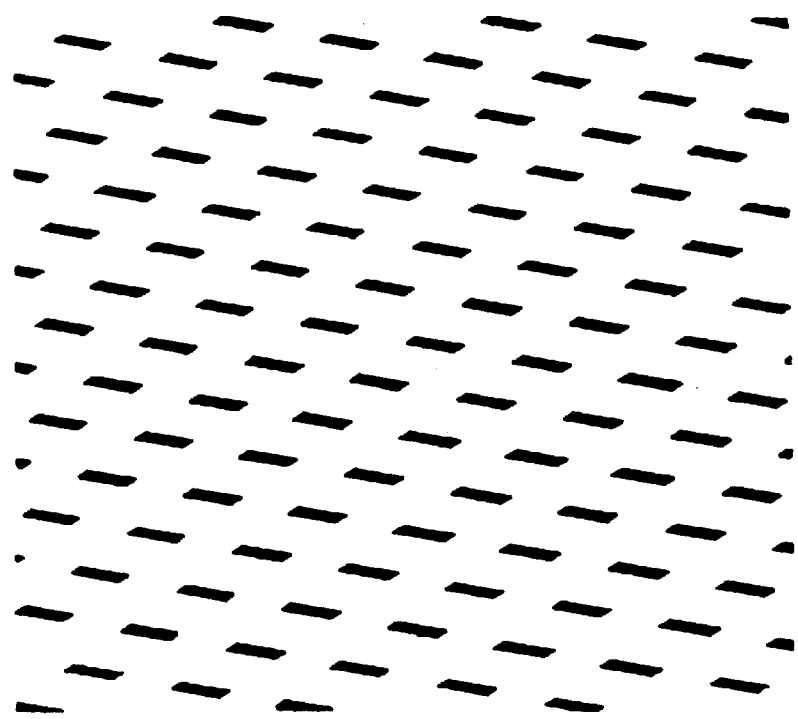

The first bonding pattern a) was in the form of small, discrete square bonding locations, as illustrated in FIG. 10, whereas the second bonding pattern b), illustrated in FIG. 11, consisted of broken lines which extended substantially in the cross-direction of the elastic band.

Both samples a) and b) were then subjected to tensile tests on a tensile stress measuring machine sold under the trademark INSTRON 1122, in order to compare their elasticities.

Each sample was tested in the following manner:

A sample having a length of 200 mm was secured firmly between the jaws of a tensile stress measuring machine sold under the trademark INSTRON 1122. The sample was stretched to a load of 10 N. The jaws were then moved towards one another until the tensile stress in the sample was 0 N. The sample was then allowed to rest for two minutes, in order to eliminate any residual stretch. The tensile stress was then again adjusted to 0 N.

Figure 12:
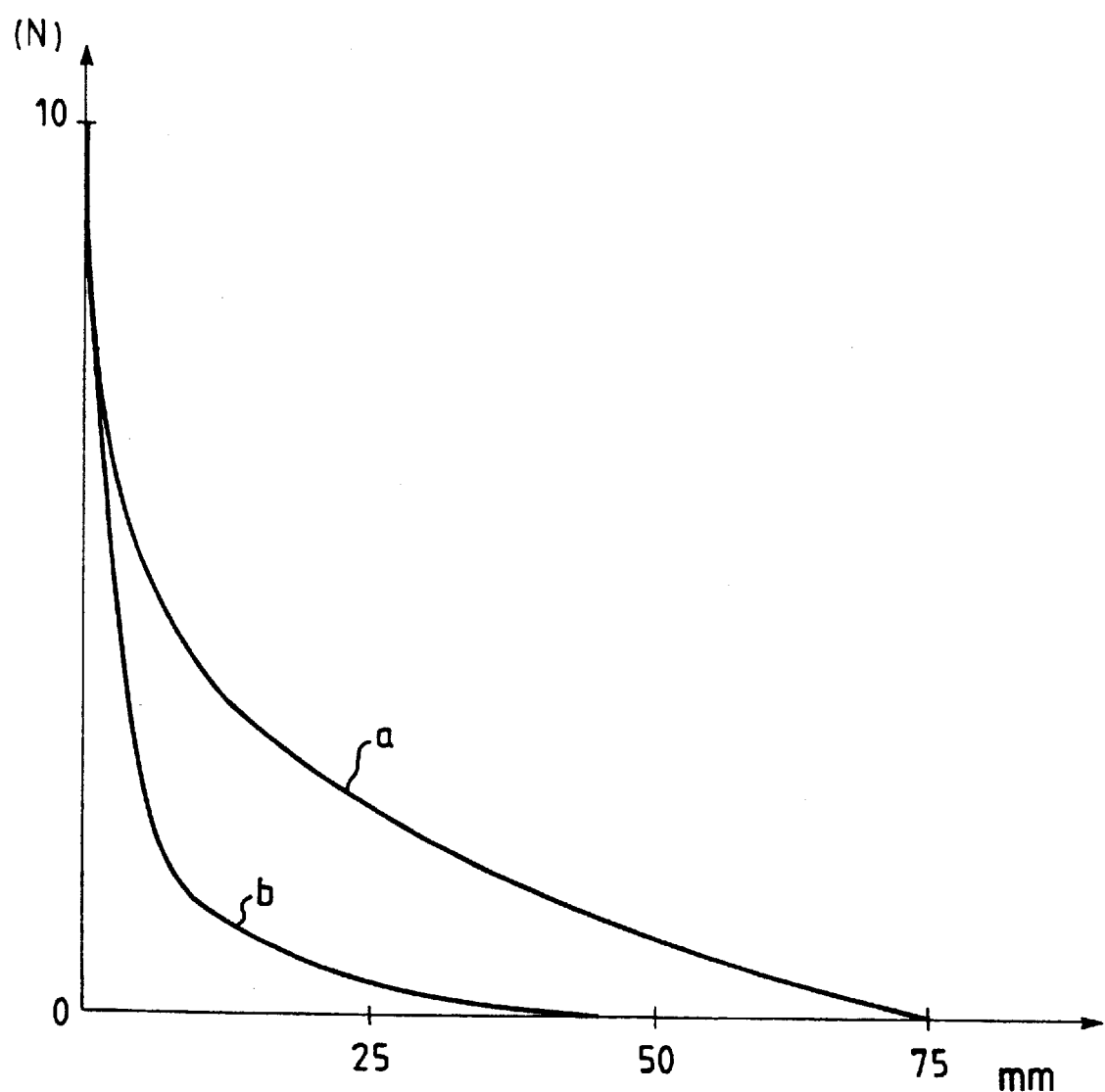
FIG. 12 is a diagram which illustrates the contraction of two elastic bands having mutually different bonding patterns.

The samples were sketched three times between the 0-level determined in the aforesaid manner and a tensile stress of 10 N. The jaws were moved together at a speed of 300 mm/min. and the sample contracting force when relaxing the tension was recorded as a function of contraction in mm. The results obtained with these samples are shown in the diagram in FIG. 12, in which each curve represents an average value of the three stretch tests carried out. The sample a) contracted through 75 mm, whereas the sample b) only contracted through 40 mm. Thus, a bonding pattern in which the bonding locations extend substantially perpendicularly to the direction in which the elastic device acts greatly reduces the elasticity of said device, whereas a punctiform bonding pattern will only slightly influence the elasticity of said device.

The total surface area of the bonds is also significant to the elasticity of the device, in addition to the configuration of the bonds and their orientation in relation to the direction in which the elastic device stretches or acts. The larger the area on the elastic device that is taken-up by the bonding locations, the smaller the degree of elasticity of said device.

Although the inventive elastic device has been described with reference to diapers it will be understood that the device can be used in a number of other applications. For instance, the invention can be applied in the manufacture of surgical dressings, protective clothing, underwear and sportsware.

Figure 13:
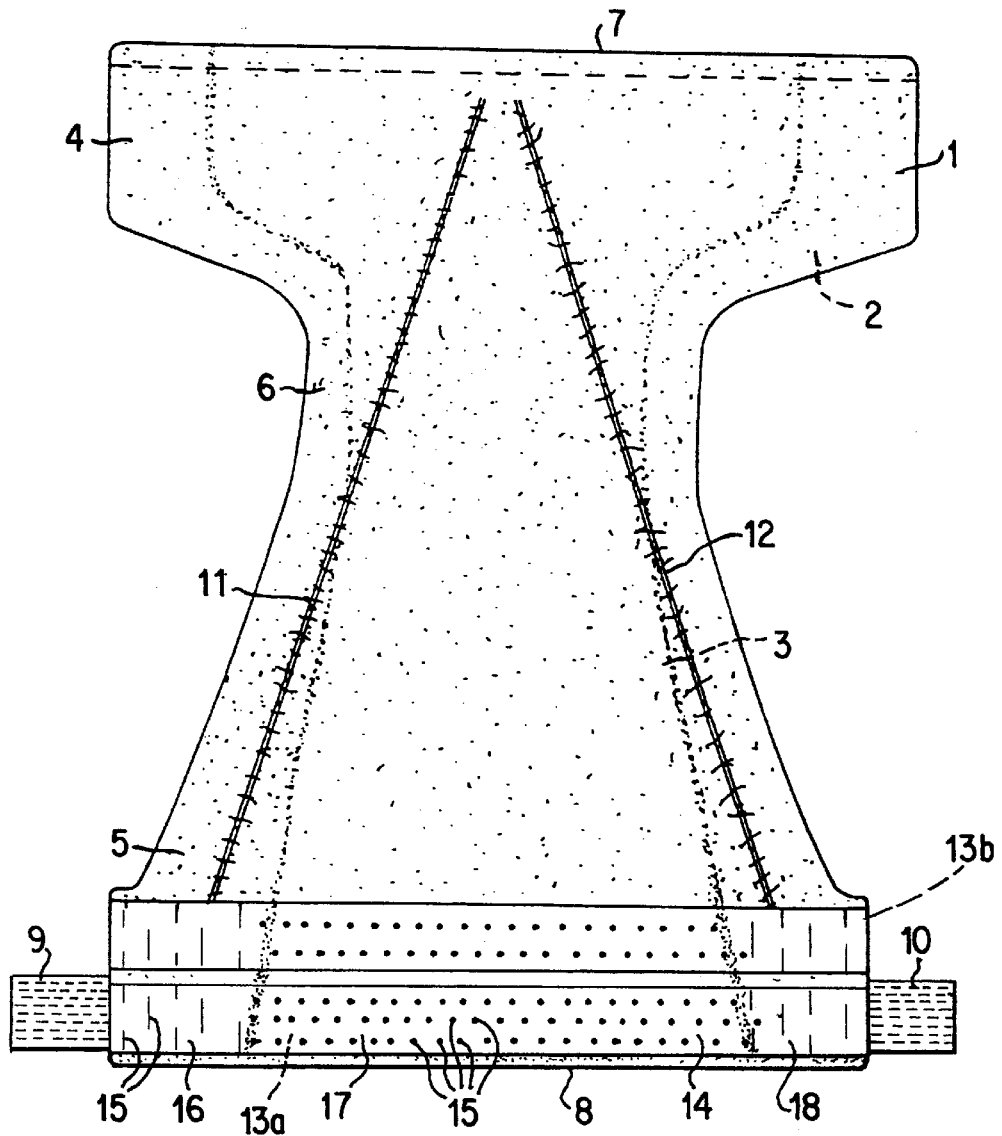
FIG. 13 illustrates a diaper similar to FIG. 1 except provided with two elastic bands.

In FIGS. 1 and 2 of the accompanying drawings, the inventive elastic device has been shown as a single elastic band. It will be understood, however, that the elastic device may consist of two or more separate bands. FIG. 13 shows an embodiment wherein the elastic device consists of two elastic bands 13a, 13b.

It will also be understood that the elastic foam material used in the exemplifying embodiments may have closed cells or may be replaced with other elastic materials, such as natural rubber, polyurethane rubber or the like. As noted in the examples above, the elastic material can be made of a polyester-based urethane foam.

The inventive elastic device can also be used to particular advantage in diapers having double leg elastication, i.e. such diapers as those in which each leg opening has an inner and an outer elastic edge. For instance, in this case, either the inner or the outer elastic edge is formed from an inventive elastic device, whereas the other elastic edge is of a conventional kind. Naturally, both edges can be provided with inventive elastic devices.

It is also conceivable to secure an inventive elastic device an the inside of a diaper, supplemented with a corresponding device of the same or a different kind on the outside of the diaper. This additional elastic device will prevent the diaper from ballooning from the wearer's body in use.

Other modifications are conceivable within the scope of the following Claims.

What is claimed is:

1. An elastic structure for use in articles which are intended for one-time use only comprising an elastic band and a material layer positioned on each side of said elastic band, said material layers being at least partially comprised of meltable material, said elastic band having perforations through all of which the material layers are joined together as a result of forming the perforations in the elastic band while stretched directly followed by joining together portions of the material layers located opposite the perforations by heat fusion, the elastic band being movable relative to the material layers.

2. An elastic structure according to claim 1, wherein the elastic band includes at least two regions having different bonding patterns and different elasticity in a direction in which the elastic band acts.

3. An elastic structure according to claim 1, wherein the elastic band includes at least one region of substantially punctiform perforations through which the two material layers are bonded together.

4. An elastic structure according to claim 1, wherein the elastic band includes at least one region with perforations which have a smaller extension in a direction in which the elastic band acts than perpendicularly to said direction and through which the two material layers are bonded together.

5. An elastic structure according to claim 1, wherein the elastic band is comprised of at least one band of elastic foam material having closed cells..

6. An elastic structure according to claim 5, wherein the foam material is a polyester-based polyurethane foam.

7. An elastic structure according to claim 1, wherein the elastic band is comprised of a plurality of separate bands of rubber material.

8. An elastic structure according to claim 1, wherein the elastic band is comprised of a plurality of separate bands of elastic foam material having open cells.

9. An elastic structure according to claim 1, wherein the elastic band is comprised of a plurality of separate bands of elastic foam material having closed cells.

10. An elastic structure according to claim 1, wherein the elastic band is comprised of at least one band of elastic foam material.

11. An elastic structure according to claim 1, wherein said elastic band is comprised of a band of rubber material.

12. A diaper comprising an absorbent pad enclosed between a liquid-permeable casing layer which is intended to face a wearer in use and a liquid-impermeable casing layer which is intended to lie remote from the wearer in use, the diaper having edges that define diaper margins, a front part which is intended to be located forwardly on the wearer in use, a rear part which is intended to be located rearwardly on the wearer in use, and a crotch part which is located between the front part and the rear part and which is intended to be placed between thighs of the wearer in use so that the diaper, when worn, embraces the lower abdomen of the wearer and therewith presents a waist margin around the waist of the wearer and a leg margin around each of the user's thighs, and including at least one elastic band which is secured in a stretched state between two material layers which are at least partially comprised of a meltable material, the at least one elastic band having perforations through all of which the material layers located on opposite sides of the at least one elastic band are bonded to one another as a result of forming the perforations while the elastic band is stretched directly followed by bonding together portions of the material layers located opposite the perforations in the stretched elastic band by heat fusion, the material layers being bonded in a bonding pattern so that the at least one elastic band is held mechanically between the material layers and so that the elastic band is movable relative to the material layers, the at least one elastic band being affixed along at least a part of at least one of the diaper margins, at least one of the material layers being joined to one of the casing layers in at least one of the diaper margins.

13. A diaper according to claim 12, wherein at least one of the material layers comprises one of the casing layers.

14. A diaper according to claim 13, wherein the liquid-permeable casing layer is folded over the at least one elastic band.

15. A diaper according to claim 13, wherein the liquid-impermeable casing layer is folded over the at least one elastic band.

16. A diaper according to claim 12, wherein the two material layers comprise a separate casing of meltable material, said separate casing being attached to one of said casing layers.

17. A diaper according to claim 12, wherein the at least one elastic band is attached at least along the waist margin of the rear part of the diaper, the diaper having fastener tabs for securing the diaper, said fastener tabs being affixed to sides of the rear part of the diaper adjacent the waist margin, the at least one elastic band having a pattern of perforations which extend substantially transversely across the at least one elastic band within regions of the waist margin at which the fastener tabs are affixed.

18. A diaper according to claim 12, including an additional elastic band affixed to each leg margin, said additional elastic bands each having at least two regions of different bonding patterns and different degrees of elasticity.

19. A diaper according to claim 18, wherein each of the additional elastic bands has at least three regions of different bonding patterns and different degrees of elasticity, one of said three regions being located in the crotch part of the diaper and having the greatest elasticity.

20. A diaper according to claim 12, including elastic devices which are attached to the diaper by gluing.

21. A diaper according to claim 12, wherein the at least one elastic band is comprised of at least one band of elastic foam material.

22. A diaper according to claim 12, further including elastic devices which are attached to the diaper by welding.

* * * * *